United States Patent [19]

Blair

[11] Patent Number: 4,976,271
[45] Date of Patent: Dec. 11, 1990

[54] BLOOD DRAWING SYSTEM

[76] Inventor: Paul A. Blair, 3621 NW. 23rd St., Lauderdale Lakes, Fla. 33311

[21] Appl. No.: 348,657

[22] Filed: May 8, 1989

Related U.S. Application Data

[63] Continuation-in-part of Ser. No. 193,059, May 12, 1988.

[51] Int. Cl.⁵ .............................................. A61B 5/00
[52] U.S. Cl. .................................. 128/764; 128/763; 604/240; 604/232
[58] Field of Search ............... 128/760, 763–766, 128/770; 604/110, 201, 232, 240, 242, 263

[56] References Cited

U.S. PATENT DOCUMENTS

| | | | |
|---|---|---|---|
| 2,437,408 | 3/1948 | Soet | 128/764 |
| 3,528,404 | 9/1970 | Chan | 128/764 |
| 4,583,974 | 4/1986 | Kokernak | 604/99 |
| 4,643,199 | 2/1987 | Jennings, Jr. et al. | 128/763 |
| 4,731,059 | 3/1988 | Wanderer et al. | 128/764 |
| 4,795,443 | 1/1989 | Permenter et al. | 604/263 |
| 4,822,343 | 4/1989 | Beiser | 128/763 |
| 4,841,985 | 6/1989 | Wanamaker | 128/770 |
| 4,846,808 | 7/1989 | Haber et al. | 128/763 |
| 4,850,374 | 7/1989 | Diaz-Ramos | 128/770 |

Primary Examiner—C. Fred Rosenbaum
Assistant Examiner—Ralph Lewis
Attorney, Agent, or Firm—Alvin S. Blum

[57] ABSTRACT

A system for use with evacuated, rubber stoppered sample tubes (3) and double-ended needles (1) facilitates blood collecting operations and prevents accidental punctures from contaminated needles after use. The tube (1) is held in a tubular cartridge (12) with a sliding control (10) for to and fro controlled motion. A holder (2) engages the mid portion of the needle (3) and the cartridge and the sliding control slides the tube onto the needle after blood vessel puncture and slides it off the needle after collection. A sliding assembly (90) positions a shield (103) at the needle point (7) and the shield is impaled upon the point so that the needle may be discarded with the point protected. A finger control (35) release the needle while avoiding exposure to the point.

10 Claims, 4 Drawing Sheets

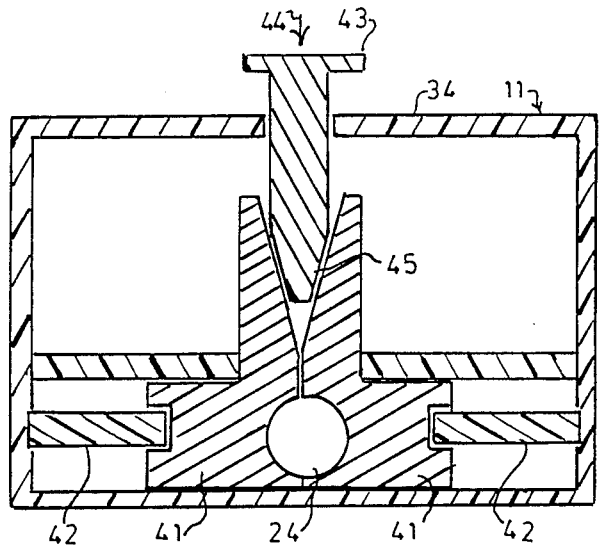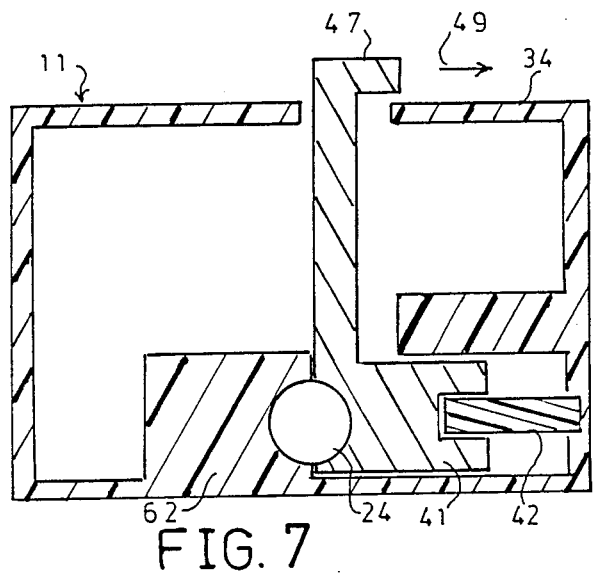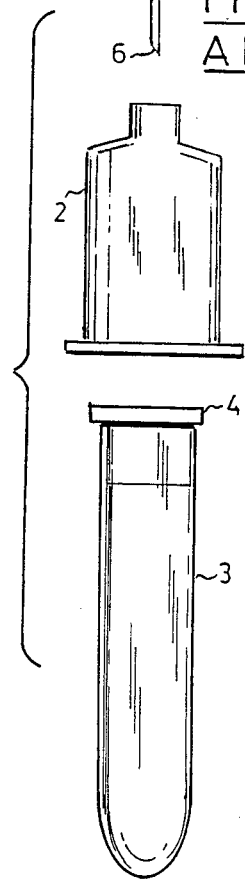
FIG. 6
FIG. 1 PRIOR ART
FIG. 7

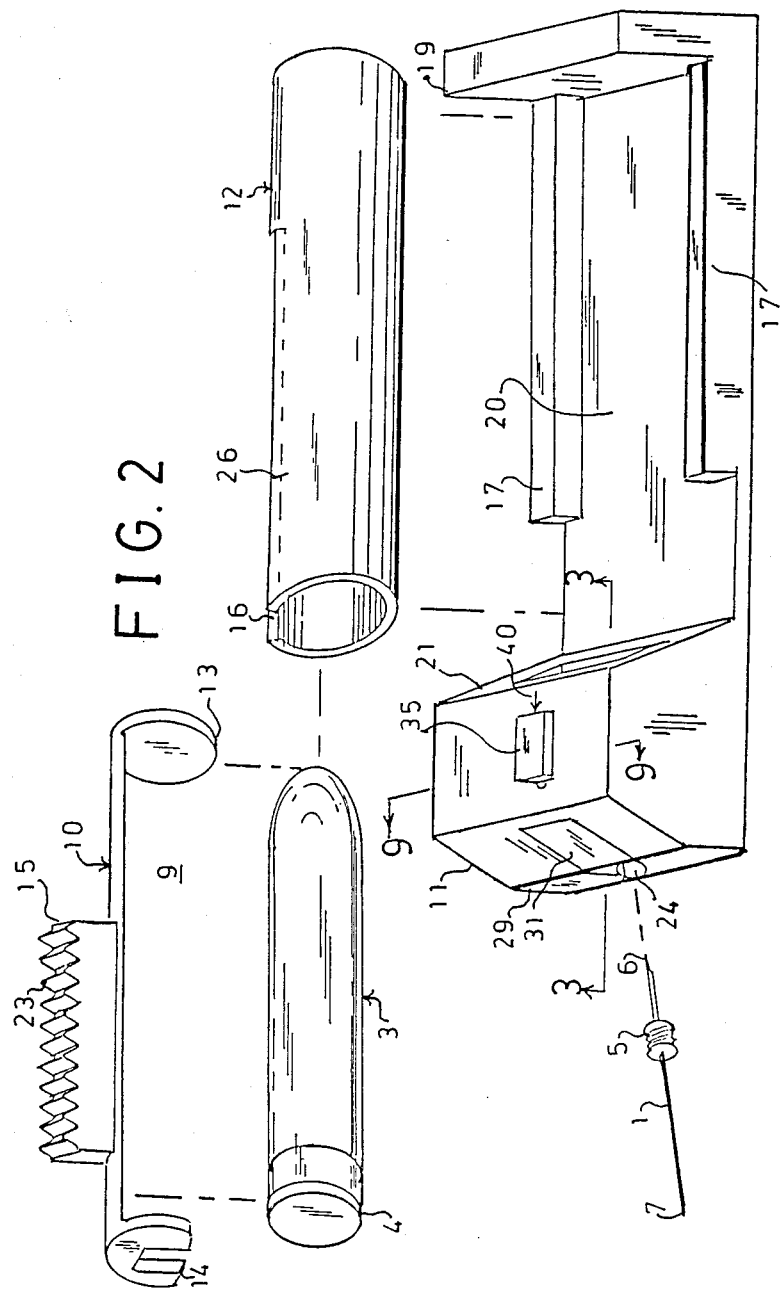

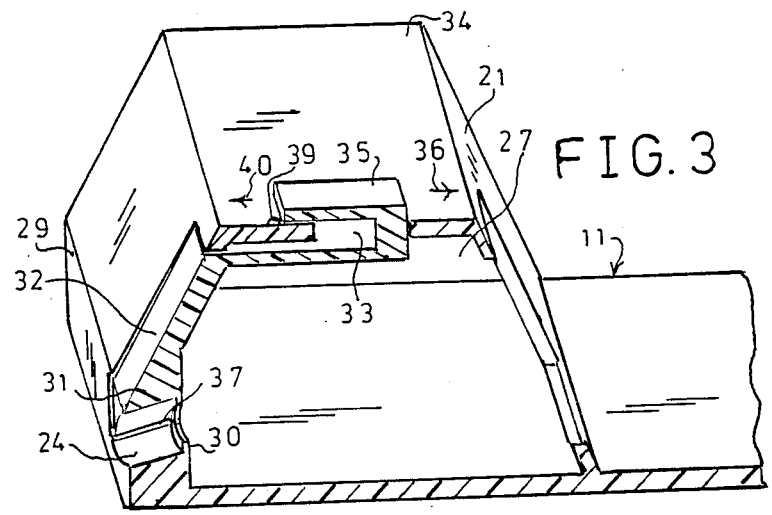
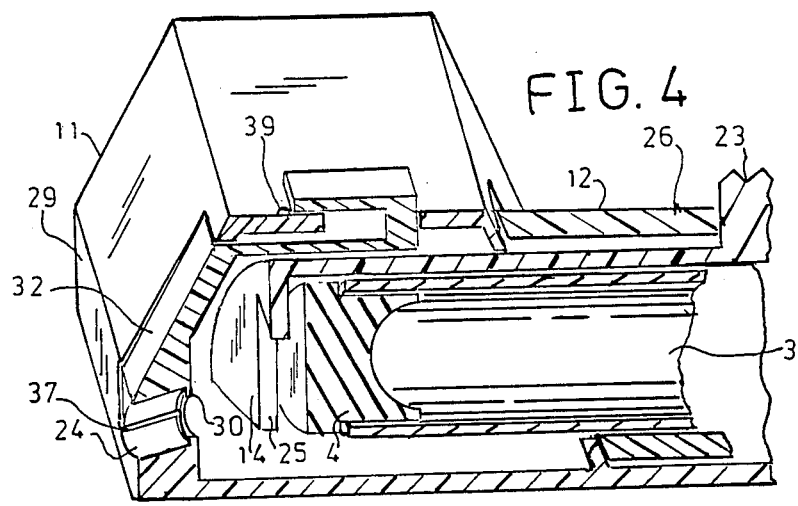
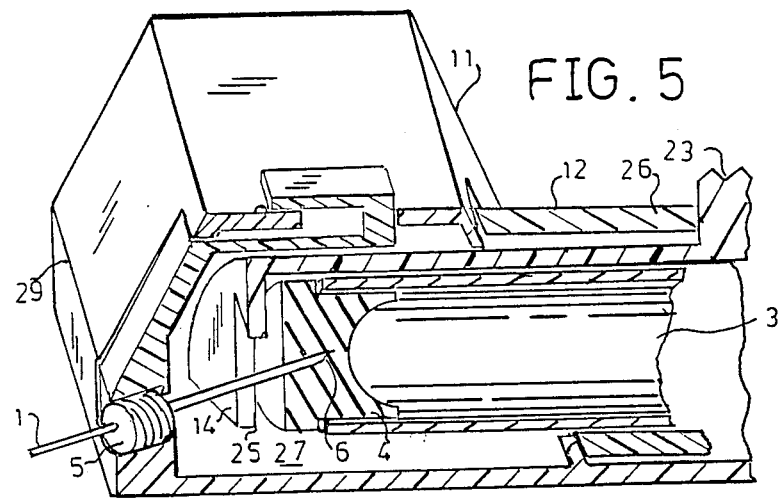

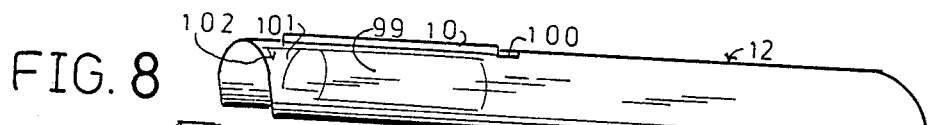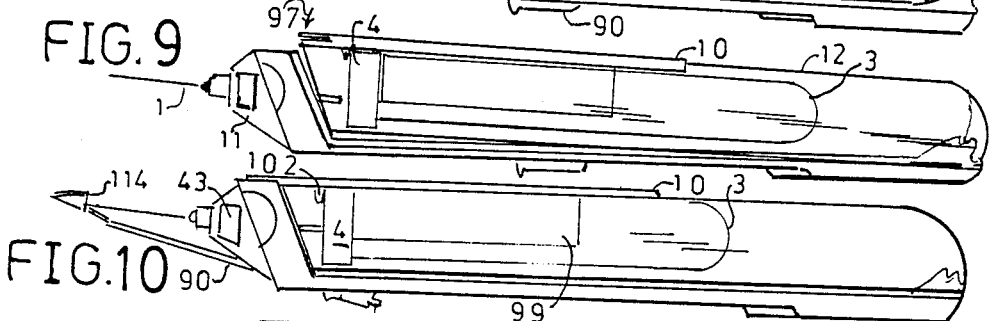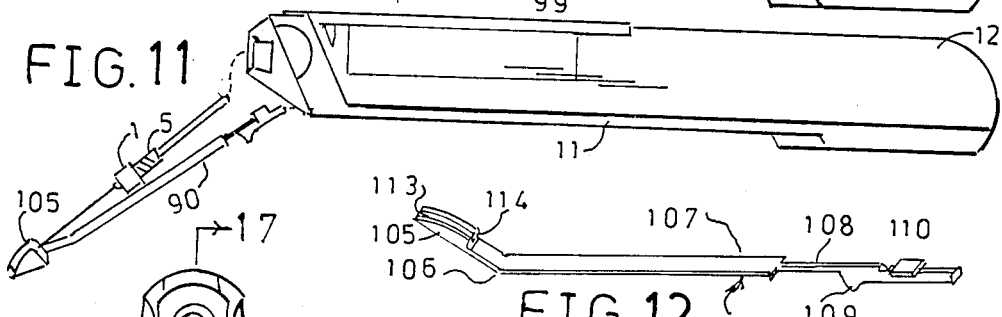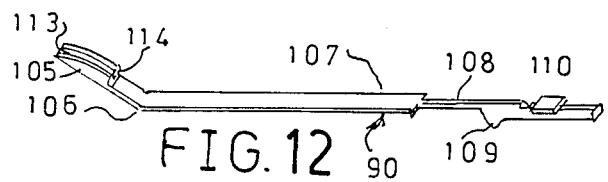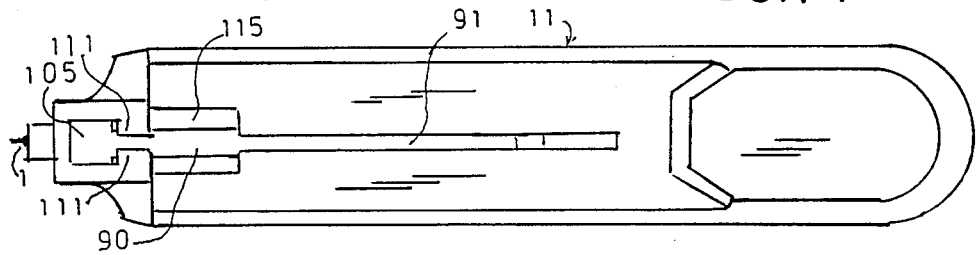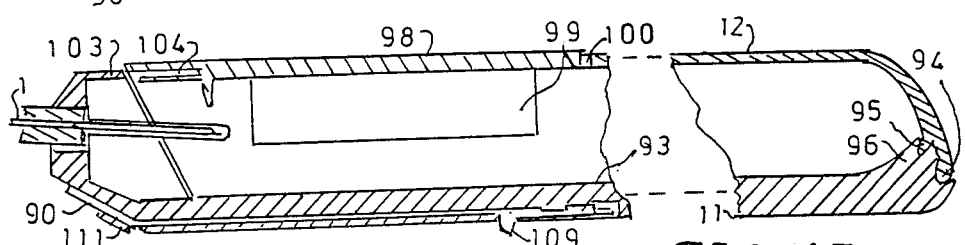

4,976,271

BLOOD DRAWING SYSTEM

This application is a continuation in part of copending patent application Ser. No. 07/193,059 filed May 12, 1988.

TECHNICAL FIELD

This invention relates to apparatus for withdrawing blood from veins and more particularly to accessories to be employed with evacuated tubes and double-ended needles to enhance their operation and safety.

BACKGROUND ART

To withdraw blood for clinical analysis, a hollow needle sealed to a syringe is used to puncture the skin and an underling vein or artery. The plunger of the syringe is slowly withdrawn as the blood fills the evacuated space between the plunger and the barrel of the syringe.

The blood is then inserted into one or more sample tubes, which may contain any of a variety of preparations to further the particular analytical procedure, including anticoagulants, preservatives and the like.

An improvement over the syringe that is in wide general use is the evacuated glass tube sealed by a rubber stopper as illustrated in FIG. 1. A double-ended needle 1 is threadably engaged by threads 5 to needle holder 2. The glass tube 3, which may contain any of the preparations to enhance analysis, contains a vacuum and is sealed by rubber stopper 4. It is inserted into needle holder 2 until the first point 6 of the needle engages, but does not fully penetrate, the rubber stopper 4. The second needle point 7 is then forced through the skin into the blood vessel. The glass tube 3 is then pushed further into needle holder 2 so that it penetrates the stopper and applied the vacuum to the point 7 inside the blood vessel, aspirating blood into the tube. The tube 3 may be withdrawn from the holder 2 and one or more additional tubes may be used to collect additional samples for additional analyses that may require different chemicals within the tube. Care must be exercised in inserting and removing tubes while the needle is in the blood vessel so that the position of needle point 7 is not disturbed by forcing it through the other wall of the vessel or removing it from the vessel or moving it laterally as it may be dislodged from its effective position or may damage the blood vessel.

When sampling is completed, the needle point 7 is removed from the arm, a covering sheath, supplied with the needle, is reapplied to the point 7 and the needle is unscrewed from the needle holder 2 and discarded. Alternatively, the needle 1 and needle holder 2 are permanently joined together and are both disposed after a single use. The needle point of the disposable needle holder must also be sheathed prior to discard because of the dangers to users from accidental skin puncture from a needle contaminated with the blood of a person who may be infected with an infectious disease that is transmitted by just such a mechanism.

DISCLOSURE OF INVENTION

It is accordingly an object of the invention to provide an improved system for withdrawing blood samples with evacuated tubes and double-ended needles that reduces the risks of accidental puncture from contaminated needles. It is yet another object of the invention to provide a system that facilitates the process of inserting and removing the tubes.

The assembly of the invention includes: a holder for a needle and cartridge; a cartridge for holding both the evacuated tube and a tube slider; and a tube slider for moving the tube relative to the cartridge toward and away from the needle in a controller manner. Means are provided for covering the point of the needle and for removing the needle from the assembly for discard that can be operated without ever moving the hand forward of the contaminated needle point to ensure both safe shielding of the point and discarding of a needle with the point covered to prevent accidental puncture during waste disposal.

These and other objects, advantages, structures and the manner through which the desired results are obtained will be best understood by reference to the accompanying drawings and detailed description.

BRIEF DESCRIPTION OF DRAWINGS

FIG. 1 is a front elevation view of the evacuated tube blood drawing assembly of the prior art.

FIG. 2 is an exploded perspective view of the blood drawing assembly of the invention.

FIG. 3 is a partial sectional view through 3—3 of FIG. 2.

FIG. 4 is a view as in FIG. 3 with the cartridge in place.

FIG. 5 is a view as in FIG. 3 with the cartridge and needle in place.

FIG. 6 is a sectional view through 9—9 of FIG. 2 showing an alternative needle-engaging mechanism.

FIG. 7 is a sectional view through 9—9 of FIG. 2 showing yet another alternative needle-engaging mechanism.

FIG. 8 is an exploded side elevation of an alternative embodiment of the blood drawing assembly.

FIG. 9 is a view as in FIG. 8 with the cartridge partially inserted.

FIG. 10 is a view as in FIG. 8 with cartridge in place and needle point covered.

FIG. 11 is a view as in FIG. 10 with needle being discarded.

FIG. 12 is a perspective view of the needle point covering member.

FIG. 13 is a front elevation view of the device of FIG. 9.

FIG. 14 is a sectional view of the device of FIG. 13 taken through the line 17—17.

FIG. 15 is a bottom view of the device of FIG. 9.

MODES FOR CARRYING OUT THE INVENTION

Referring now first to FIGS. 2, 3, 4 and 5, the evacuated tube 3 is inserted into the space 9 of tube slider 10, between the push end 13 and the pull end 14. The loaded tube slider 10 is then inserted into cartridge 12 with projection 15 on slider 10 passing through slot 16 on upper surface of cartridge 12. The loaded cartridge 12 is then inserted into holder 11. The side elevations 17 and rear elevation 19 are at right angles to the base 20 of holder 11. The first elevation 21 meets base 20 at a sloping angle corresponding to the sloping angle of the front end 22 of cartridge 21 so that the cartridge 12 cannot be inserted incorrectly into the holder and so that it is held snugly in holder 11 during the phlebotomy or blood drawing process.

Projection 15 on slider 10 has serrations 23 on its upper surface for engaging the finger of the operator to slide the slider 10 and its tube 3 to and from within the cartridge 12 in place on holder 11. A double-ended needle 1 is removably engaged in aperture 24 of holder 11 by threaded portion 5 as best seen in FIG. 5. As tube 3 is pushed forward, its rubber stopper 4 is impaled by the first point 6 of needle 1 which passes through slot 25 of puller 14 on slider 10. The needle point 6 has not yet penetrated the evacuated space of tube 3, yet it is sealed off by the rubber stopper. This is the preferred condition for initiating the insertion of the needle through the skin and into the blood vessel. If the needle point is not sealed off by the rubber, blood will pass out of the needle point and around the outside of the tube. If the needle point enters the evacuated space before puncturing the skin, air will enter the tube and, since it has no means of escape, will occupy space that cannot be filled with blood. The invention provides better control over establishing this condition of partial puncture, including an index marker 26 on cartridge 12 to indicate when projection 15 on slider 10 has advanced the tube 13 to that extent inside the chamber 27 at the front end of holder 11. After the needle point 7 has penetrated the skin, the slider 10 is pushed all the way forward, causing needle point 6 to enter the evacuated space. After blood is collected, the slider 10 is moved in the opposite direction, causing its pulling end 14 to pull the stopper off the needle and fully within the cartridge 12. The cartridge 12 may then be removed and replaced with another cartridge if another sample is to be collected before the needle is withdrawn from the patient.

An important aspect of the invention is the means by which the needle 1 is held in holder 11 during phlebotomy, the means by which the needle point is covered after use, and the seams whereby the contaminated needle is subsequently removed without exposing the operator to the hazards of accidental puncture. The needle point covering embodiment is shown in FIGS. 8-15. Three alternative embodiments of the needle holding means are shown, the first in FIGS. 2-5. The threaded portion 5 of needle 1 is engaged by aperture 24 at the front end 29 of holder 11. This aperture may have smooth walls as shown or may have a female thread matching the threads 5 on needle 1. A ridge 30 at the rear of aperture 24 limits penetration of the needle. The aperture 24 is defined by a lower half that is part of the fixed body of the holder 11 and an upper half that is part of a sliding member 31 that slides rectilinearly in slot 32 at front 29 of holder 11 and slot 33 at top 34 of holder 11. Sliding member 31 extends up above top 34 of holder 11 at finger projection 35. In the position shown, finger projection 35 has been moved fully to the rear in direction of arrow 36 in slot 33 to the needle locked position. The two halves of aperture 24 have a sloping interface 37 that provides a wedge effect pulling both halves together tightly around the threaded portion 5 of needle 1 and holding it securely in place. A small, rounded elevation 39 acts as a detent against the underside of the finger projection 35 which is springy, causing the sliding member to be locked in this position, to release the needle for disposal after use, the finger projection is forced forward in the direction of arrow 40, whereupon the projection 35 springs up over detent 39, the wedge at aperture 24 opens up as sliding member 32 moves forward out of slot 32 in the front face 29 of holder 11. An alternative needle holding mechanism is shown in FIG. 6. The needle holding aperture 24 is defined by two sliding members 41 which are pushed together in the closed position shown by spring elements 42. These spring elements are polyurethane rods.

When pushbutton 43 in top 34 of holder 11 is pushed downward as indicated by arrow 44 is spreads apart the sliding members 41 by inclined plane action of its lower wedge portion 45, opening up the orifice 24 to release the needle held therein.

In the alternative embodiment of a needle holding mechanism illustrated in FIG. 7, the sliding member 41 forms one half of needle holding aperture 24 and the other half is formed by a fixed member 46 that is fixed to holder 11. Spring element 42 holds the aperture 24 closed. Slide control 47 in top 34 of holder 11 is forced laterally in the direction shown by arrow 49 to slide member 41 laterally opening up aperture 24 to release the needle. In all three embodiments the needle is released by a control that can be operated without getting the hands near the contaminated needle point.

As best seen in FIGS. 2 and 5, the needle 1 slopes downward from its engagement with the holder 11 to provide a more convenient angle for skin puncture.

Referring now to FIGS. 8-15, a preferred embodiment of the blood drawing system is shown that provides for a less expensive cartridge 12 that can hold evacuated tubes 3 of various sizes without adjustment. It also provides a needle point covering member 90 that slides fore and aft in a slot 91 in the base of holder 11.

The cartridge 12 is open at the bottom and its two long edges 92 straddle a central elevation 93 of holder 11 to restrict lateral motion. At the rear of cartridge 12 a lower projection 94 and an upper projection 95 engage and interlock with matching recesses in ridge 96 of base 11 to provide a quick and easy means of loading and unloading the cartridge 12 onto the holder 11 by first engaging this rear interlock mechanism and then tilting the front end of the cartridge into position. This is best shown in FIG. 9 with arrow 97 indicating how front end is tilted into place after the rear end of the cartridge is engaged on ridge 96 of the holder 11. The tube slider 98 slides in a slot 100 on top of the cartridge 12 as described above for other embodiments. The tube slider includes a flexible, C-shaped tube clip 99 that will removably snap into place around evacuated tube 3 of various sizes. A forward ridge 102 together with clip 99 define a recess 101 that engages the rubber stopper 4 to hold the tube securely during fore and aft movements of the slider to impale the stopper 4 on the inner point 6 of the needle 1 for sampling and to remove the stopper from the needle after sampling. The anterior portion of the slider 98 has a recess 104 separating it into an upper member and lower member. When the cartridge is in place on the holder and the slider is pushed forward to pierce the stopper, the upper wall 103 of the holder fits into the recess 104, effectively locking the cartridge 12 in place so that it cannot be lifted out of holder 11 until the slider with its tube is retracted from the needle point 6.

The mechanism for covering the sharp point 7 of the needle after use and before discarding to prevent accidental puncture with a contaminated needle includes the disposable needle point covering member 90 shown in FIG. 12 before insertion in housing 11. It includes a head portion 105 a flat strip portion 107 with an angle bend 106, a narrow portion 108, a flange 110 and a pushbutton 109. As best seen in FIGS. 10-15, the needle covering member 90 slides in slot 91 in underside of housing 11 with the flange 110 and the flat strip portion 107 being wider than the slot 91 to prevent member 90 from dropping through the slot. The upwardly sloping portion 112 of the holder 11 contains the needle holding mechanism described above with a pushbutton 43 that releases the needle. Two tabs 111 on the sloping portion 112 of the holder hold the portion of covering member 90 that is anterior to the bend 106. After the covering member 90 is installed in the slot in the housing, the needle is installed. After the blood sampling is completed, the needle point is covered and the needle discarded, as follows:

The pushbutton 109 on covering member 90 is pushed forward. The tabs 111 bend the flat strip portion 107 of the member 90 upward until the head portion 105 impinges on, and slides along, the needle shaft as the covering member 90 moves forward, the channel 113 in head 105 centering on the shaft. When the ridge 114 on head 105 passes the needle point, a snapping of the springy covering member 90 is heard and felt. The pushbutton is now pulled back slightly. This forces the needle point 7 into the ridge 114, safely covered in point. Now the needle release button 43 is pressed, and the needle discarded. The narrow portion 108 of member 90 passes through the space between tabs 111 to free the anterior portion of member 90 and the flange 110 moves into the enlarged portion 115 of slot 91 to free the rear of the covering member (best seen in FIG. 15) so that the needle 1 and covering member 90 drop away together. The user never positions a hand in front of the needle point during this process so that there is not change of accidental puncture.

INDUSTRIAL APPLICABILITY

The invention is applicable to the drawing of blood from humans and animals where a faster, easier system with reduced danger from infection is desired. The skill required for use is less than with systems of the prior art, which may permit less skilled individuals to perform the task.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made without the underlying idea or principles of the invention within the scope of the appended claims.

I claim:

1. A system for safely withdrawing blood samples with an evacuated tube sealed by a pierceable rubber stopper and a double-ended needle having a middle portion, the improvement comprising:
   (a) a holder means for removably holding said needle and a cartridge means in position for withdrawing blood;
   (b) tube sliding means for sliding said tube onto said needle through said stopper in a first sliding motion and for sliding said tube away from said needle in a second sliding motion, said sliding means slidable relative to said holder means and said cartridge means;
   (c) cartridge means for removably enclosing said tube and said sliding means therein in position for providing said first and said second motion by finger control of said sliding means when said holder is holding said cartridge means; and
   (d) needle engaging means connected to said holder means for securely engaging said needle in position for phlebotomy in cooperation with said tube and needle releasing means for releasing said needle after use, wherein said needle releasing means is operable from behind the exposed point of said needle to prevent accidental contact with said point after it is contaminated with blood.

2. The system according to claim 1 in which said needle engaging means includes detent means for locking said needle in engaged position during use.

3. The system according to claim 1 in which said needle engaging means includes an aperture means for engaging said mid-portion of said needle, said aperture means defined by two half-cylinders and said needle releasing means includes means for moving at least one of said half-cylinders away from the other.

4. The system according to claim 3 in which said aperture means has a female thread means for threadably engaging said mid-portion of said needle.

5. The system according to claim 3 including spring bias means for holding said half-cylinders together.

6. The system according to claim 3 in which wedge means hold said two half-cylinders together.

7. The system according to claim 1 in which said sliding means includes indexing means for indicating when said tube means has been advanced to the position wherein said needle has its point completely embedded in said stopper but not penetrating through said stopper.

8. The system according to claim 1, further including needle point covering means removably held by said holder means in a forward and backward sliding engagement, said covering means including a head portion and a body portion, and said holder means further includes guide means for guiding said head portion forcefully against the shaft of said needle as said body portion is extended forward until said head portion passes said exposed point to enable said head portion to be impaled upon said exposed point when said covering means is then moved backward.

9. A needle holder for safely employing for skin puncture a needle having a connecting portion, a shaft portion and an exposed point, said holder comprising:
   (a) a needle engaging mean connected to said holder to securely hold said connecting portion to deploy said exposed point in position for skin puncture;
   (b) means in said holder to receive and slide a collection tube into communication with said needle;
   (c) needle point covering means including a head portion and an elongate body portion;
   (d) sliding engagement means in said holder for slidably holding said body portion of said needle covering means in forward and backward sliding engagement relative to said needle engaging means; and
   (e) guide means in said holder for forcefully guiding said head portion against said shaft portion as said body portion is extended forward until said head portion passes said exposed point to enable said point to impale said head portion when said body portion is then moved backward.

10. The holder according to claim 9 in which said needle engaging means removably holds said connecting portion of said needle including needle releasing means and in which said sliding engagement means includes means for releasing said needle covering means when said needle is released from said holder.

* * * * *